(12) United States Patent
Nord et al.

(10) Patent No.: US 8,744,148 B2
(45) Date of Patent: Jun. 3, 2014

(54) METHOD AND APPARATUS REGARDING ITERATIVE PROCESSES AS PERTAIN TO MEDICAL IMAGING INFORMATION

(75) Inventors: Janne Nord, Espoo (FI); Benjamin Haas, Wabern (CH); Thomas Coradi, Zurich (CH)

(73) Assignee: Varian Medical Systems International AG, Zug (CH)

( * ) Notice: Subject to any disclaimer, the term of this patent is extended or adjusted under 35 U.S.C. 154(b) by 549 days.

(21) Appl. No.: 12/862,365

(22) Filed: Aug. 24, 2010

(65) Prior Publication Data

US 2012/0051607 A1  Mar. 1, 2012

(51) Int. Cl.
*G06K 9/00* (2006.01)
(52) U.S. Cl.
USPC .......................................................... 382/128
(58) Field of Classification Search
None
See application file for complete search history.

(56) References Cited

U.S. PATENT DOCUMENTS

| 7,146,380 | B2 | 12/2006 | Schaepe et al. | |
|---|---|---|---|---|
| 2005/0113961 | A1* | 5/2005 | Sabol et al. | 700/182 |
| 2008/0063301 | A1* | 3/2008 | Bogoni et al. | 382/294 |
| 2008/0080788 | A1 | 4/2008 | Nord et al. | |
| 2010/0061611 | A1* | 3/2010 | Xu et al. | 382/131 |

OTHER PUBLICATIONS

Audette et al. "An Algorithmic Overview of Surface Registration Techniques for Medical Imaging;" Medical Image Analysis 4; 2002, 17 pages.
Crum et al. "Non-rigid image registration: theory and practice;" The British Journal of Radiology 77; 2004, 14 pages.
Droske et al., "Multi scale Joint segmentation and registration of Image morphology;" University of California, Los Angeles; 2005, 14 pages.
Fornefett et al., "Elastic Medical Image Registration Using Orientation Attributes at Landmarks;" In E. Berry, D. Hogg, K V. Mardla, M. A. Smith (Eds.), University of Leeds, 1998; 4 pages.
Franaszek et al. "Hybrid Segmentation of Colon filled with Air and Opacified Fluid for CT Colonography;" IEEE Transactions on Medical Imaging 25 (3); 2006; 11 pages.
Gui et al., "A Variational Framework for the Simultaneous Segmentation and Object Behavior Classification of Image Sequences;" Signal Processing Institute (ITS), Ecole Polylechnique Federale de Lausanne (EPFL), Lausanne, Switzerland; 2007; 12 pages.
Han et al., "A Variational Framework for Joint Image Registration, Denoising and Edge Detection;" Universities Erlangen-Nornberg, Bonn, and California; 2006; 5 pages.

(Continued)

*Primary Examiner* — Elaine Gort
*Assistant Examiner* — Gregory Lultschik
(74) *Attorney, Agent, or Firm* — Fitch, Even, Tabin & Flannery LLP

(57) ABSTRACT

A medical-imaging digital-computing platform serves to access a plurality of data objects and to execute an iterative process with respect to these data objects. The data objects themselves each at least generally pertain to portions of the human anatomy and may comprise, for example, both a source data object and a target data object. The platform executes the iterative process to determine at least one of a labeling of a portion of one of the data objects and a geometric relationship between at least portions of at least two of the data objects. This can be done, for example, by automatically employing both a segmentation module and a registration module as steps within the iterative process. This can also comprise determining when to automatically generate an intermediate data object to provide as input to at least one of these modules.

17 Claims, 3 Drawing Sheets

(56) References Cited

OTHER PUBLICATIONS

Han et al., "Atlas-Based Auto-segmentation of Head and Neck CT Images;" Lecture Notes in Computer Science 5242, Proc. 11th Int. Conf. Medical Image Computing and Computer-Assisted Intervention (MICCAI), Part II, 2008; 8 pages.

Hellier et al., "Coupling Dense and Landmark-Based Approaches for Non Rigid Registration;" INRIA Rennes, France; 2000; 27 pages.

Huang et al., "Metamorphs: Deformable Shape and Appearance Models;" Lehigh University, Bethlehem, PA, USA, and Rutgers University, New Brunswick, NJ; 2008; 35 pages.

Lorenzen et al., "Multi-Modal Image Set Registration and Atlas Formation;" Medical Image Analysis Jun. 2006, 10(3), 2006; 12 pages.

Metaxas et al., "Hybrid Deformable Models for Medical Segmentation and Registration;" IEEE ICARCV 1-4244-0342-1/06; 2006; 6 pages.

Park et al., "Construction of an Abdominal Probabilistic Atlas and its Application in Segmentation;" IEEE Transactions and Medical Imaging 22 (4); 2003; 10 pages.

Periaswamy et al., "Medical Image Registration with Partial Data;" Siemens Medical Solutions USA, Inc., Malvern, PA 19355, USA, and Dartmouth College, Hanover, NH 03755, USA; 2005; 25 pages.

Pohl et al., "A Unifying Approach to Registration, Segmentation, and Intensity Correction;" Med Image Comput Assist Interv; 8(pt 1); 2005; 11 pages.

Rohlfing et al., "Quo Vadls, Atlas-Based Segmentation?;" In J. Suri, D. L. Wilson, and S, Laxminarayan (eds.), The Handbook of Medical Image Analysis: Segmentation and Registration Models, Kluwer; 2007; 57 pages.

\* cited by examiner

METHOD AND APPARATUS REGARDING ITERATIVE PROCESSES AS PERTAIN TO MEDICAL IMAGING INFORMATION

TECHNICAL FIELD

This invention relates generally to the processing of medical-imaging information and more particularly to iterative processes in these regards.

BACKGROUND

The generation of interior images of humans and other living creatures comprises a well understood area of endeavor. High-energy particles and beams are often used in these regards, for example, to form both two and three-dimensional images of interest. Such images, in turn, often serve a medical purpose. This can include, for example, diagnosing a particular ailment or condition, conducting a surgery-related assay of a given patient, and so forth.

The sheer volume of such information, coupled with economic interests to limit an expert's time interpreting such information, prompts the use of automated systems to interpret or otherwise pre-process medical images of this sort. In some cases this can comprise generally matching or registering, to some extent possible, an image in question with one or more other images. These other images may be earlier images for the same patient or may be images (individually or in some aggregated fashion) of other patients.

As another example in these regards, this can comprise automatically segmenting a given image. Generally speaking, segmenting refers to parsing one or more objects in an image to separate one object from another. Segmenting can also include parsing a given object into two or more constituent components, parts, or the like. By one approach, segmenting comprises labeling such objects/parts with corresponding alphanumeric identifiers (such as anatomical monikers, references, or the like).

Iterative processes are often employed to embody such an automated process. An iterative process begins with some approximation (or guess) and cycles through a series of successive approximations to test for a better solution. In some cases, the iterative process of choice is segmentation based. In this case, a technique based on rules and standard image processing operations (see, for example, co-owned U.S. patent application Ser. No. 11/494,860 entitled ANATOMIC ORIENTATION IN MEDICAL IMAGES as filed on Jul. 28, 2006, the full and entire contents of which are hereby incorporated by this reference) is used to extract the outline of an anatomical structure in a target or destination image. As one simple illustrative example in this regard, the bony tissue in a target image can be labeled by extracting all image pixels above a certain intensity level.

In other cases, the iterative process of choice is registration based. In this case, typically points of interest within the source image are matched to corresponding points in the target image in an attempt to make a point-by-point registration for all points within the source image.

Generally speaking, these approaches are separately used for any of a variety of image types and between any of a variety of sources and targets. These approaches are also sometimes employed with more general models of anatomic structure.

For all their value, however, there is room for improvement. In some application settings these known approaches can be unduly computationally intensive. This, in turn, can require an amount of processing time that is unacceptable in a clinical setting and/or computational capacity that is economically unfeasible. The alternative, of course, may be to accept a processing result that is too course or rough for present needs.

BRIEF DESCRIPTION OF THE DRAWINGS

The above needs are at least partially met through provision of the method and apparatus regarding iterative processes as pertain to medical imaging information described in the following detailed description, particularly when studied in conjunction with the drawings, wherein.

Figure 1:
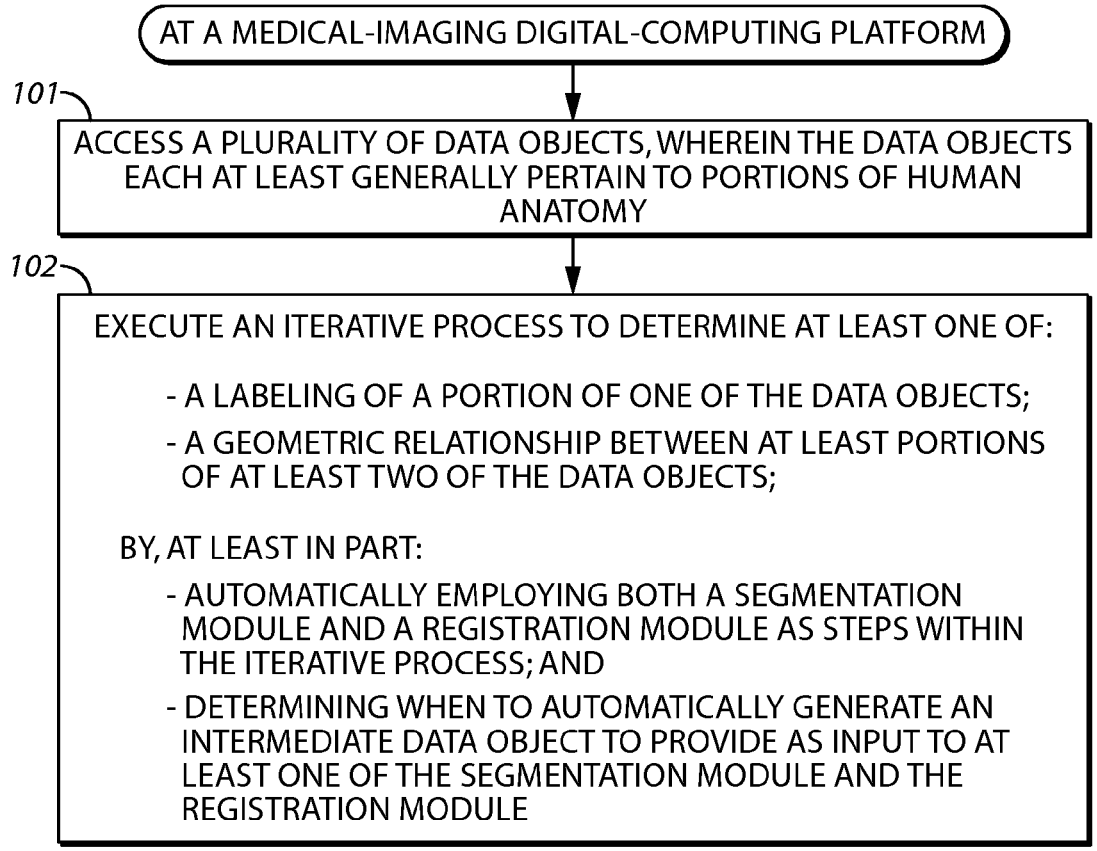
FIG. 1 comprises a flow diagram as configured in accordance with various embodiments of the invention.

Elements in the figures are illustrated for simplicity and clarity and have not necessarily been drawn to scale. For example, the dimensions and/or relative positioning of some of the elements in the figures may be exaggerated relative to other elements to help to improve understanding of various embodiments of the present invention. Also, common but well-understood elements that are useful or necessary in a commercially feasible embodiment are often not depicted in order to facilitate a less obstructed view of these various embodiments of the present invention. Certain actions and/or steps may be described or depicted in a particular order of occurrence while those skilled in the art will understand that such specificity with respect to sequence is not actually required. The terms and expressions used herein have the ordinary technical meaning as is accorded to such terms and expressions by persons skilled in the technical field as set forth above except where different specific meanings have otherwise been set forth herein.

DETAILED DESCRIPTION

Generally speaking, pursuant to these various embodiments, a medical-imaging digital-computing platform serves to access a plurality of data objects and to execute an iterative process with respect to these data objects. The data objects themselves each at least generally pertain to portions of the human anatomy and may comprise, for example, both a source data object and a target data object. The platform executes the iterative process to determine at least one of a labeling of a portion of one of the data objects and a geometric relationship between at least portions of at least two of the data objects. This can be done, for example, by automatically employing both a segmentation module and a registration module as steps within the iterative process. This can also comprise determining when to automatically generate an intermediate data object to provide as input to at least one of these modules.

The aforementioned activity of automatically determining which of the modules to employ during a given step within the iterative process can comprise, by one approach, determining which of the segmentation module and the registration module to employ during this given step. This determination, in turn, can be based, if desired, upon the results of a prior step in the iterative process.

This determination regarding when to automatically generate an intermediate data object to provide as input to one of these modules can comprise, at least in part, determining when a given one of the data objects should be converted into a form that is compatible with a selected one of the segmentation module and the registration module. As other examples in these regards, such a determination can be based upon determination of when a combination of information (such as a combination of logical information or geometric information) will be useful or necessary.

So configured, an iterative process that appropriately makes use of both segmentation and registration-based approaches can be employed when processing, for example, a source medical image with a target medical image to provide a resultant comparison therebetween. In many cases these teachings will yield either a better result than many prior teachings and/or will yield a satisfactory result in a shorter period of time (presuming comparable computational capacity).

These and other benefits may become clearer upon making a thorough review and study of the following detailed description. Referring now to the drawings, and in particular to FIG. 1, an illustrative process 100 that is compatible with many of these teachings will now be presented.

This process 100 can be carried out by and at a medical-imaging digital-computing platform of choice. In some cases, a general purpose computer (such as a so-called personal computer (PC) may suffice. In other cases, a more elaborate computer (for example, a multiprocessor workstation) may be appropriate to meet the requirements of a given application setting.

This process 100 provides the step 101 of accessing a plurality of data objects. These data objects each at least generally pertain to portions of human anatomy. For many application settings these data objects will comprise, at least in part, both a source data object and a target data object. The source data object, for example, can comprise an image of some portion of a given patient's body. The target data object, in turn, can comprise another image from this same patient or from a different person. These teachings will also accommodate using content representing a surrogate (for example, an image obtained by statistical operation from a population of patients).

Generally speaking, for many application settings the target data object(s) will comprise one or more medical images. These teachings will accommodate a wide variety of modalities by which such medical images are initially captured or represented. Examples in these regards include, but are not limited to, computed tomography (CT), magnetic resonance imaging (MRI), positron emission tomography (PET), x-ray images, ultrasound, infrared, and any number of other image-capturing technologies involving various forms and frequencies of high frequency energy. Such modalities are all well understood in their respective areas of practice.

Still speaking generally, and again for many application settings, the source data objects can comprise one or more of a medical image, at least one anatomic label, and/or one or more anatomic model. This reference to anatomic labels will be understood to refer to a direct or indirect reference to an alphanumeric string that particularly identifies an object (such as an organ, tissue, bone, or a man-made item (such as a pacemaker, a fastener such as a surgical screw, an artificial joint, a marker, or the like), to note but a few examples), or a part of an object, within the human body. This can comprise the formal medical taxonomic expression for such an object (or object portion) or a more common anatomical expression as desired.

This plurality of source data objects can comprise, if desired, a plurality of medical images from the group consisting of medical images for a same human being or medical images for a plurality of different human beings. These teachings will accommodate other possibilities, combinations, and permutations in these regards as well.

This step 101 can comprise acquiring some or all of these data objects at a particular time of need. This step 101 can also comprise acquiring some or all of these data objects well prior to this time of need (for example, hours, days, weeks, months, or even years prior to accessing these data objects as per this step 101). The particular approach observed in a given application setting will likely depend, at least in part, upon the requirements and/or opportunities as tend to characterize a given application setting.

Generally speaking, these data objects will themselves comprise digital data files at the time of being accessed as per this step 101. These files can comprise compressed or uncompressed files as desired. These files can also comprise encrypted or unencrypted files as desired. There is no particular requirement that these files all share a same file type so long as the medical-imaging digital-computing platform is able to carry out the functionality described herein.

At step 102 the medical-imaging digital-computing platform executes an iterative process. This iterative process serves to determine at least one of a labeling (such as an anatomical labeling) of a portion of one of the data objects and/or a geometric relationship between at least portions of at least two of the data objects (such as a source data object and a target data object). Generally speaking, the particular form of the informational deliverable will likely be selected by an end user or might be fixed by an administrator or even the original programmer. These teachings will also accommodate, however, permitting the iterative process itself to select the nature of the informational output if desired. For example, in some application settings it may be useful to permit the process 100 to select the specific form of the determined result based upon some criterion of interest (such as a most-accurate result).

The process 100 achieves this result, at least in part, by automatically employing both a segmentation module and a registration module as steps within the iterative process. These references to "modules" will be understood to refer to computational processes that, when executed, yield a corresponding labeling or registration result respectively. Accordingly, these modules may each therefore comprise one or more software or firmware routines or subroutines or may also comprise, in whole or in part, a fixed hardware-based algorithm.

This can comprise, by one approach, automatically determining which of these modules to employ during a given step within the iterative process. This decision can be based, for example, upon the results of a prior step in the iterative process. For example, when a prior step in the iterative process yields a result suggesting that present analysis of the available information using a segmentation approach may be useful, this step can comprise deciding to presently use the segmentation module when effecting the next iteration of the iterative process.

These teachings will also accommodate making this determination based upon other criteria as well, if desired (either alone or in combination with the foregoing). For example, the process 100 can base this determination upon predefined rules that apply to a particular detected portion of a human being's anatomy. To illustrate, when aware that the portion at issue comprises a human being's kidney, this inquiry can be configured to favor a segmentation approach over a registration approach.

As another example, this determination can be based upon patient information (such as specific information regarding the patient's age, condition, diagnosis, prescribed treatment, secondary ailments or conditions, and so forth), a predefined scheme, or even user input (as entered, for example, by a user of the medical-imaging digital-computing platform such as a medical technician).

As yet another example in these regards, this determination can be based upon prior module-based success or failure during a prior step of the iterative process. As one simple illustration in these regards, when a just-previous iteration using the registration module seemingly yielded a considerably improved result, it may be useful to elect to again utilize the registration module to see if a significant improvement will again result.

This process 100 can also accommodate supporting this step 102 by determining when to automatically generate an intermediate data object to provide as input to at least one of the segmentation module and the registration module. This can comprise, by one approach, determining when a given one of the data objects should be converted into a form that is compatible with a selected one of the aforementioned modules. The precise nature of this conversion will of course vary with the specific needs of a given implementation. As one specific and non-limiting example in these regards, this step may comprise creating a binary image of segmented structures using white points against a background of black points (where such a binary image may be useful to compatibly suit the limitations and/or requirements of a given registration module). As another specific and non-limiting example, this step may comprise using a deformation field (obtained, for example, using a registration module) to extract landmarks from an atlas to thereby provide landmarks that are compatible with a given segmentation module. And as yet another specific and non-limiting example, this step may comprise generating a region of interest from previously-generated information using margin and Boolean operators to provide a region of interest that is compatible with a plurality of modules while limiting the processing volume.

As will be shown below in more detail, such intermediate data objects can serve as a useful mechanism to facilitate the aforementioned use of both segmentation and registration processes in a single iterative process. By one approach, these segmentation and registration modules can provide, as a corresponding output, an intermediate data object that can then serve as the input (or the basis for the input) of a subsequent iterative step. As one illustrative example in these regards, the segmentation module can determine, at least in part, an anatomical labeling of an intermediate data object that comprises a medical image. As another illustrative example, the registration module can determine, at least in part, at least one geometric relationship between two or more intermediate data objects that comprise medical images.

Figure 2:
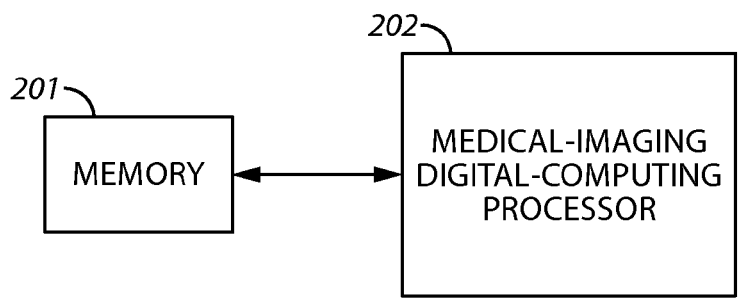
FIG. 2 comprises a block diagram as configured in accordance with various embodiments of the invention.

The above-described processes are readily enabled using any of a wide variety of available and/or readily configured platforms, including partially or wholly programmable platforms as are known in the art or dedicated purpose platforms as may be desired for some applications. Referring now to FIG. 2, an illustrative approach to such a platform will now be provided.

In this illustrative example, the apparatus 200 comprises a memory 201 that operably couples to a medical-imaging digital-computing processor 202. This memory 201 can serve to store, for example, the aforementioned data objects (including, as desired, the aforementioned intermediate data objects). This memory 201 can also serve to store executable digital computer instructions that, when executed by the medical-imaging digital-computing processor 202, cause the latter to effect one or more of the steps, actions, and/or functions described herein. It will be understood that this memory 201 can comprise a single discrete element as suggested by the illustration, or can comprise a plurality of discrete elements that may or may not be collocated with one another.

The medical-imaging digital-computing processor 202 can comprise a fixed-purpose hard-wired platform or can comprise a partially or wholly programmable platform. All of these architectural options are well known and understood in the art and require no further description here. It will also be understood that additional components can be readily accommodated as desired, including but not limited to an end-user input mechanism (such as a keyboard, a cursor-control mechanism, a touch screen, a voice-recognition mechanism, and so forth), an end-user output mechanism (such as one or more displays, a printer, an acoustic transducer, and so forth), or the like.

Such an apparatus 200 may be comprised of a plurality of physically distinct elements as is suggested by the illustration shown in FIG. 2. It is also possible, however, to view this illustration as comprising a logical view, in which case one or more of these elements can be enabled and realized via a shared platform. It will also be understood that such a shared platform may comprise a wholly or at least partially programmable platform as are known in the art.

Figure 3:
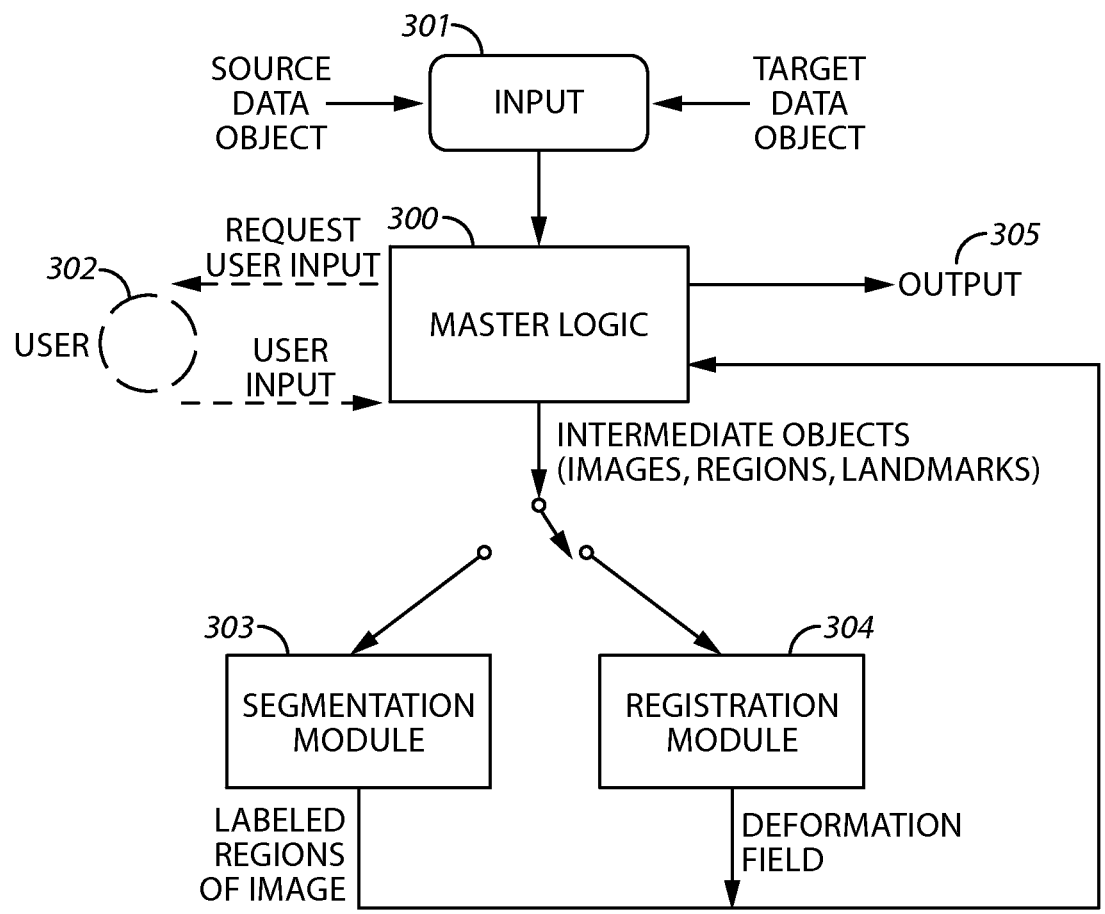
FIG. 3 comprises a block diagram as configured in accordance with various embodiments of the invention.

Referring now to FIG. 3, a more particular instantiation of the functionality of such a medical-imaging digital-computing processor 202 will be presented. Using this approach, the medical-imaging digital-computing processor 202 employs master logic 300 to carry out the described process 100. Accordingly, the master logic 300 receives input 301 comprising the aforementioned data objects.

More particularly, this input 301 comprises at least one source data object (such as, for example, one or more medical images, one or more sets of labels that define one corresponding anatomic structures, one or more anatomic models (such as an anatomic atlas, an anatomic statistical surrogate, an anatomic math representation, and so forth), or the like. This input 301 also comprises one or more target data objects. For many application settings these target data objects will comprise medical images. (It will be understood that the medical images as comprise the input 301 may or may not share a common capture and/or rendering/expression modality.)

As alluded to earlier, this input 301, in whole or in part, can be captured or otherwise accessed at the time of need (for example, at the time of exercising the aforementioned iterative process) or can be previously stored and held pending a need for the information.

The master logic 300 itself can be configured to run in a more-or-less fully automated fashion. In the alternative, if desired, the master logic 300 can be configured to interact with a user 302. This can comprise, for example, presenting the user 302 with a request for user input and receiving the requested user input. Such an approach might be appropriate, for example, when a clear choice cannot be automatically drawn between a segmentation-based approach and a registration-based approach as a next iterative step.

The master logic 300, generally speaking, serves to determine whether to employ a segmentation module 303 or a registration module 304 as a next step in an iterative process to correlate at least one source data object with at least one target data object. The master logic 300 can also serve, as noted above, to determine when to provide for preparation of an intermediate data object that can then be presented to the selected module. These intermediate data objects can themselves be formed using output deliverables from the segmentation and/or registration modules 303 and 304 and/or one or more of the input objects. These intermediate data objects can be used as so provided or, if desired, can be modified in form or substance by the master logic 300 to suit some particular need or opportunity.

Generally speaking, the segmentation module 303 provides one or more labeled regions of a medical image as output. Such regions may be single points as well. The registration module 304, in turn, provides one or more deformation fields as pertain to medical images. Both modules may also output numerical values (scores) estimating the reliability of a labeling or registration step or activity, respectively.

At the conclusion of the iterative process, the master logic 300 provides corresponding output 305. This output can vary as desired to suit a particular need. By one approach this output 305 can comprise registration information that associates (for example, pixel by pixel) a given source image (or a set of such images) with a given target image. By another approach this output 305 can comprise segmentation information. In this case, the output 305 may specifically comprise an appropriately labeled target image.

Figure 4:
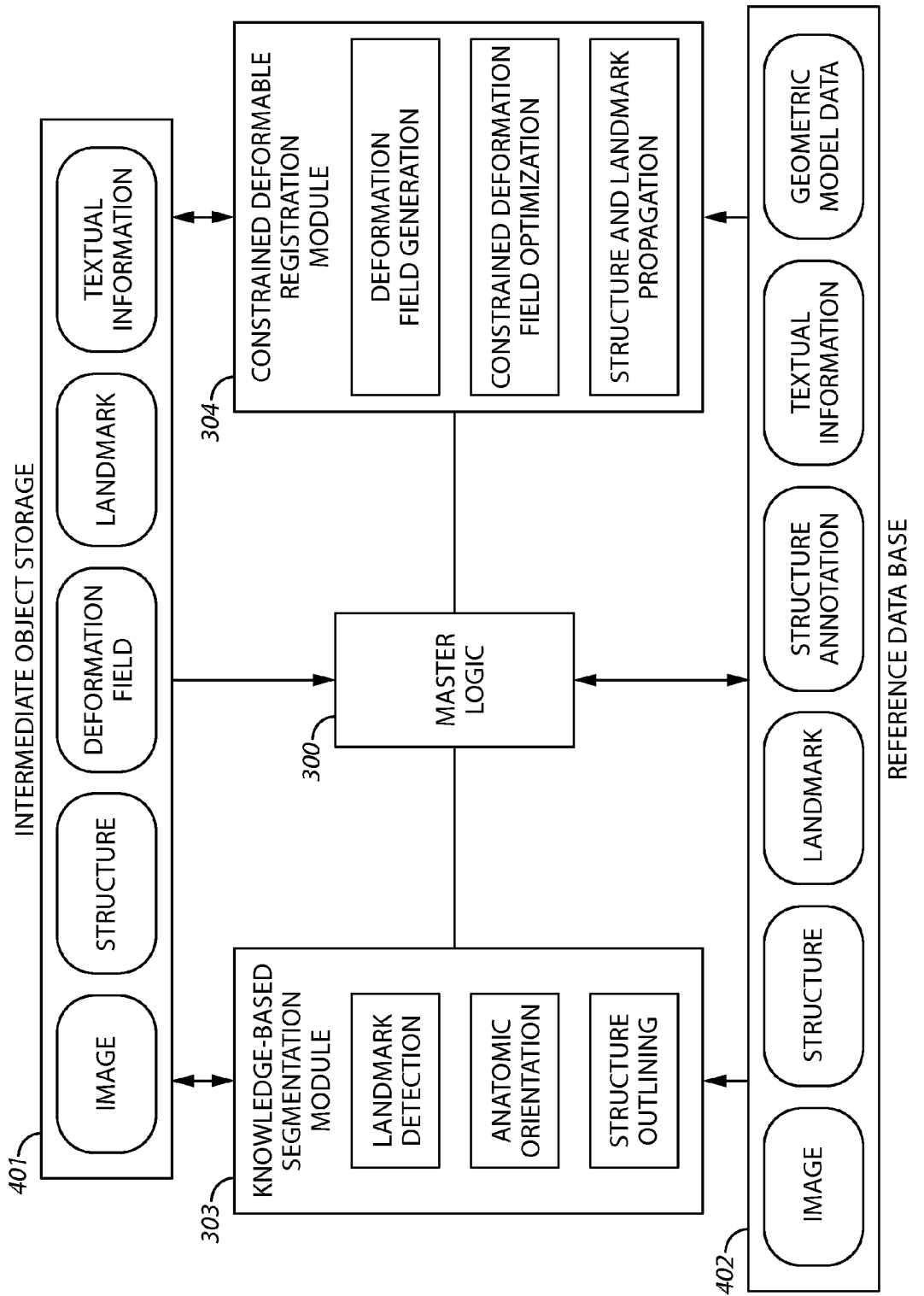
FIG. 4 comprises a block diagram as configured in accordance with various embodiments of the invention.

Referring now to FIG. 4, further details in these regards will be presented.

In this illustrative example, an intermediate object storage 401 (using, for example, the previously-described memory) serves to store the aforementioned intermediate data objects as the iterative process cycles to conclusion. FIG. 4 illustrates that these teachings will accommodate a wide range of forms and modalities for these intermediate data objects. Specific illustrated examples include (but are not limited to) images, structural information, deformation fields, landmarks (as may pertain, for example, to both natural structures as well as man-made objects that are placed upon or embedded within a given human being in order to provide a spatial reference point for these purposes), and even textual information.

FIG. 4 also illustrates that the master logic 300 as well as the aforementioned modules can access a reference data base 402. This reference data base 402 can similarly store a variety of different kinds or formats of information. Illustrated examples include images, structures, landmarks, structure annotations, textual information, and geometric model data. Depending upon the needs of a given application setting, some of the source data objects utilized by the described process 100 may comprise items from this reference data base. (It will again be understood that the contents of this reference data base may comprise a logical whole or may be distributed over a plurality of local and/or remote resources.)

In this illustrative example, the segmentation module 303 comprises a knowledge-based segmentation module. More particularly, this knowledge-based segmentation module is configured to perform landmark detection, determine anatomic orientation, and perform structure outlining. These functions are well understood in the art and require no further elaboration here.

The registration module 304, in turn, comprises (in this illustrative example) a constrained deformable registration module. More particularly, this constrained deformable registration module is configured to generate deformation fields, conduct constrained deformation field optimization, and effect structure and landmark propagation. Again, these functions are each well understood in the art. By way of example, constraints to the "constrained deformable registration module" can be fixed points (points that are not to be moved), regions of interest, or spatially variant elasticity parameters.

So configured, the described platform and process are able to process a given target image with respect to one or more source data objects to support a variety of medical activities including both diagnostic and therapeutic services. More particularly, these teachings permit such processing to make selective and automatic use of both segmentation methodologies and registration methodologies in an iterative approach to thereby attain the benefit of the strengths of both methodologies while offering the opportunity to temper the less desirable aspects of their usage. This can yield better results and/or results that are attained more quickly given a particular computational base.

As but one illustrative example in these regards, and without intending any limitations with respect to the specifics of this example, these teachings can be readily applied with respect to outlining thoracic structures of interest in CT and PET images for radiotherapy planning. In this case the enabling platform can start with having a segmentation module find the patient's lungs, trachea, thoracic aorta, and spinal canal. Then, after selecting an appropriate already-segmented reference image (such as, for example, an atlas image) from a reference database, the implementing platform could use a deformable registration module to map the CT image to the selected atlas image.

A deformation algorithm may then use image information for both images and information about structures that have been defined in both images. For example, the enabling platform can force matches for specific structures such as bones, lungs, and so forth. After forming a corresponding deformation field, other structures (such as the esophagus, vertebrae, and parasternal lymph nodes) can be propagated from the atlas image.

Multiple registration steps producing deformation fields relating several reference images or models with an actual CT image may be used to transfer specific anatomic regions of interest. For example, esophagus and vertebrae images may be transferred from different atlas images as appropriate.

In any event, after the structure information has been transferred, the segmentation module may serve to refine the structures based on a priori information. Using the structures defined so far, the segmentation module may also find more landmarks. Then, the master logic may find another appropriate atlas image and the deformation module may be used again to register a region of interest and propagate more structures from this atlas image, and so on.

These teachings are also leverageable in any number of ways. As but one illustrative example, one or more of the data objects can comprise an anatomical model. As used herein, this reference to "model" will be understood to refer to any variety of model, including but not limited to image-based models, a text or rule-based description of anatomical facts, or even a collection of simple geometric shapes (such as spheres, cylinders, cubes, and so forth) that are described in analytical form.

Those skilled in the art will recognize that a wide variety of modifications, alterations, and combinations can be made with respect to the above described embodiments without departing from the spirit and scope of the invention, and that such modifications, alterations, and combinations are to be viewed as being within the ambit of the inventive concept.

We claim:

1. A method comprising:
   by a medical-imaging digital-computing processor:
   the processor accessing a memory to obtain a plurality of data objects, wherein at least some of the data objects each comprises a medical image that pertains to portions of human anatomy;
   the processor executing an iterative medical-imaging process that comprises starting with an initial approximation and cycling through a series of successive approximations to test for a better solution to determine at least one of:

a labeling of a portion of one of the data objects; and
a geometric relationship between at least portions of at least two of the data objects;
by, at least in part:
the processor automatically employing both a segmentation module and a registration module as steps within the iterative process by, at least in part, automatically selecting between employing the segmentation module and the registration module during a given iteration of the iterative process, wherein the segmentation module and the registration module are separate modules from one another and during the given iteration either the segmentation module or the registration module is employed, but not both; and
the processor determining when to automatically generate an intermediate data object having a form that is compatible with the selected module to provide as input to at least one of the segmentation module and the registration selected module.

2. The method of claim 1 wherein the plurality of data objects comprise, at least in part, both a source data object and a target data object.

3. The method of claim 2 wherein the target data object comprises a medical image.

4. The method of claim 2 wherein the source data objects comprise at least one of:
a medical image;
at least one anatomic label;
an anatomic model.

5. The method of claim 4 wherein the source data objects comprise a plurality of medical images from the group consisting of:
medical images for a same human being;
medical images for a plurality of different human beings.

6. The method of claim 1 wherein determining when to automatically generate an intermediate data object to provide as input to at least one of the segmentation module and the registration module comprises, at least in part, determining when a given one of the data objects should be converted into a form that is compatible with a selected one of the segmentation module and the registration module.

7. The method of claim 1 wherein the segmentation module determines, at least in part, an anatomical labeling of an intermediate data object comprising, at least in part, a medical image.

8. The method of claim 1 wherein the registration module determines, at least in part, at least one geometric relationship between at least two intermediate data objects comprising, at least in part, medical images.

9. The method of claim 1 wherein automatically selecting between employing the segmentation module and the registration module during a given iteration of the iterative process comprises making this automatic selection, at least in part, based upon results of a prior step in the iterative process.

10. The method of claim 1 wherein automatically selecting between employing the segmentation module and the registration module during a given iteration of the iterative process comprises, at least in part, making the automatic selection based upon at least one of:

predefined rules applying to a detected portion of a human being's anatomy;
patient information;
a predefined scheme;
prior module-based success during a prior step of the iterative process.

11. An apparatus comprising:
memory;
a medical-imaging digital-computing processor operably coupled to the memory and configured to:
access the memory to access a plurality of data objects, wherein the data objects each comprises a medical image that pertains to portions of human anatomy;
execute an iterative medical-imaging process that comprises starting with an initial approximation and cycling through a series of successive approximations to test for a better solution to determine at least one of:
a labeling of a portion of one of the data objects;
a geometric relationship between at least portions of at least two of the data objects;
by, at least in part:
automatically employing both a segmentation module and a registration module as steps within the iterative process by, at least in part, automatically selecting between employing the segmentation module and the registration module during a given iteration of the iterative process, wherein the segmentation module and the registration module are separate modules from one another and during the given iteration either the segmentation module or the registration module is employed, but not both; and
determining when to automatically generate an intermediate data object having a form that is compatible with the selected module to provide as input to at least one of the segmentation module and the registration selected module.

12. The apparatus of claim 11 wherein the plurality of data objects comprise, at least in part, both a source data object and a target data object.

13. The apparatus of claim 12 wherein the target data object comprises a medical image.

14. The apparatus of 12 wherein the source data objects comprise at least one of:
a medical image;
at least one anatomic label;
an anatomic model.

15. The apparatus of claim 14 wherein the source data objects comprise a plurality of medical images from the group consisting of:
medical images for a same human being;
medical images for a plurality of different human beings.

16. The apparatus of claim 11 wherein the segmentation module determines, at least in part, an anatomical labeling of an intermediate data object comprising, at least in part, a medical image.

17. The apparatus of claim 11 wherein the registration module determines, at least in part, at least one geometric relationship between at least two intermediate data objects comprising, at least in part, medical images.

* * * * *

UNITED STATES PATENT AND TRADEMARK OFFICE
CERTIFICATE OF CORRECTION

PATENT NO.         : 8,744,148 B2                                           Page 1 of 1
APPLICATION NO.    : 12/862365
DATED              : June 3, 2014
INVENTOR(S)        : Janne Nord, Benjamin Haas and Thomas Coradi It is certified that error appears in the above-identified patent and that said Letters Patent is hereby corrected as shown below:

IN THE CLAIMS:
Claim 14, column 10, line 42, after "of" insert --claim--.

Signed and Sealed this
Second Day of September, 2014

Michelle K. Lee
*Deputy Director of the United States Patent and Trademark Office*